(12) United States Patent
Ngo-Chu

(10) Patent No.: US 10,456,519 B2
(45) Date of Patent: Oct. 29, 2019

(54) APPARATUS AND METHOD FOR IRRIGATING SINUS CAVITY

(71) Applicant: Acclarent, Inc., Irvine, CA (US)

(72) Inventor: Don Q. Ngo-Chu, Irvine, CA (US)

(73) Assignee: Acclarent, Inc., Irvine, CA (US)

(*) Notice: Subject to any disclaimer, the term of this patent is extended or adjusted under 35 U.S.C. 154(b) by 199 days.

(21) Appl. No.: 15/293,745

(22) Filed: Oct. 14, 2016

(65) Prior Publication Data

US 2018/0104404 A1   Apr. 19, 2018

(51) Int. Cl.

| A61M 3/02 | (2006.01) |
|---|---|
| A61M 25/00 | (2006.01) |
| A61M 1/00 | (2006.01) |
| A61M 25/10 | (2013.01) |
| A61M 29/02 | (2006.01) |
| A61B 17/24 | (2006.01) |
| A61B 17/22 | (2006.01) |

(52) U.S. Cl.
CPC ........... A61M 3/0283 (2013.01); A61B 17/24 (2013.01); A61M 1/0058 (2013.01); A61M 25/0041 (2013.01); A61M 25/10 (2013.01); A61M 29/02 (2013.01); A61B 2017/22067 (2013.01); A61B 2217/005 (2013.01); A61M 2025/0004 (2013.01); A61M 2025/1013 (2013.01); A61M 2025/1052 (2013.01); A61M 2025/1061 (2013.01); A61M 2029/025 (2013.01); A61M 2210/0618 (2013.01); A61M 2210/0681 (2013.01)

(58) Field of Classification Search
CPC .. A61M 2210/0681; A61M 2210/0618; A61M 2025/0004; A61M 2025/1052; A61M 2025/1013; A61M 2025/1061; A61M 25/10; A61M 25/0041; A61M 3/0283; A61M 1/0058; A61M 29/02; A61B 17/14; A61B 2017/22067; A61B 2217/005
See application file for complete search history.

(56) References Cited

U.S. PATENT DOCUMENTS

| 5,447,497 | A | 9/1995 | Sogard et al. | |
|---|---|---|---|---|
| 8,251,942 | B1 * | 8/2012 | Al-Rashdan | A61M 25/10 |
| | | | | 604/101.01 |
| 9,050,440 | B2 * | 6/2015 | Becker | A61M 3/0295 |
| 9,155,492 | B2 | 10/2015 | Jenkins et al. | |

(Continued)

FOREIGN PATENT DOCUMENTS

WO   WO 2015/028798 A1   3/2015

OTHER PUBLICATIONS

International Search Report and Written Opinion dated Jan. 11, 2018 for International Application No. PCT/US2017/055689, 12 pages.

*Primary Examiner* — Nathan R Price
*Assistant Examiner* — Anh Bui
(74) *Attorney, Agent, or Firm* — Frost Brown Todd LLC

(57) ABSTRACT

An apparatus includes a flexible catheter which may have a plurality of lumens extending from a proximal end to a distal end, a suction opening in fluid communication with a first lumen, a plurality of irrigating openings in fluid communication with a second lumen, a dilator in fluid communication with a third lumen and an occluding balloon in fluid communication with the fourth lumen. The catheter may be used to dilate an ostium, occlude the ostium, irrigate a sinus, and suction a sinus.

12 Claims, 12 Drawing Sheets

(56) References Cited

U.S. PATENT DOCUMENTS

| | | |
|---|---|---|
| 9,408,955 B2 | 8/2016 | Jenkins et al. |
| 2008/0183128 A1 | 7/2008 | Morriss et al. |
| 2010/0030031 A1 | 2/2010 | Goldfarb et al. |
| 2010/0241155 A1 | 9/2010 | Chang et al. |
| 2011/0004057 A1 | 1/2011 | Goldfarb et al. |
| 2014/0074141 A1 | 3/2014 | Johnson et al. |
| 2015/0290438 A1* | 10/2015 | Gerrans ............... A61B 5/6853 600/435 |
| 2016/0310041 A1 | 10/2016 | Jenkins et al. |

* cited by examiner

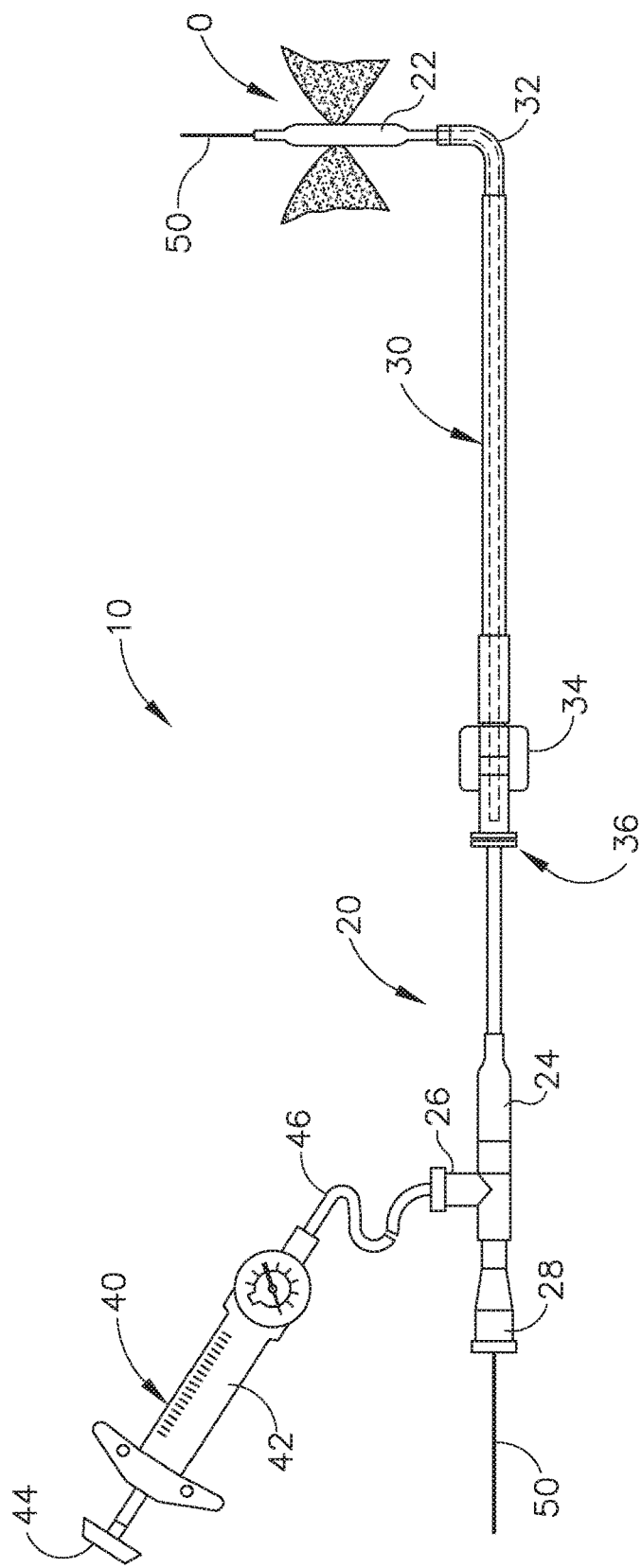

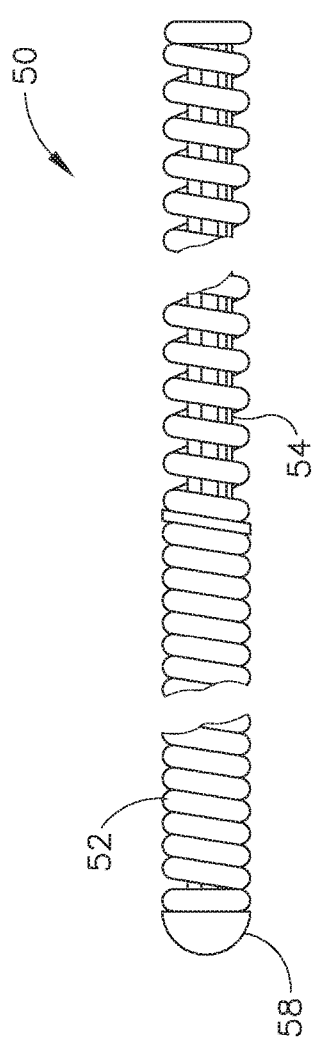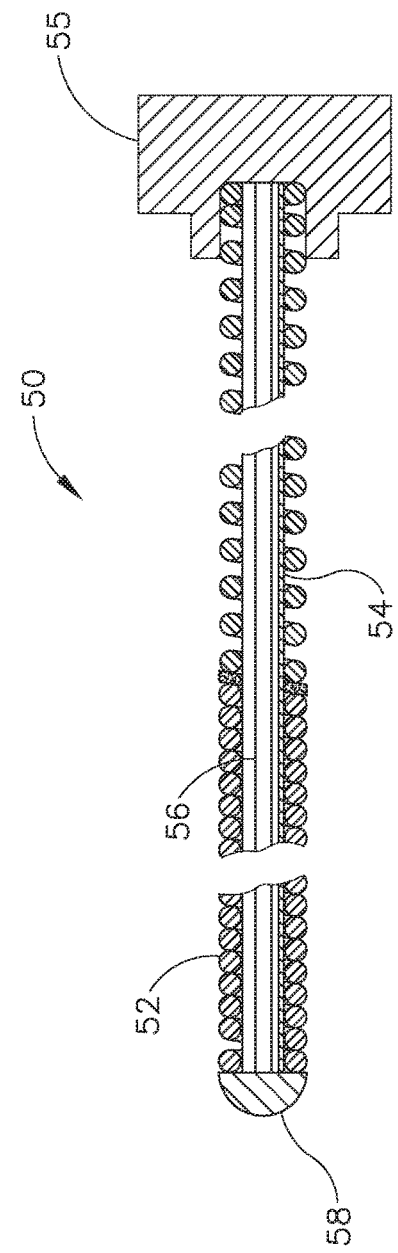

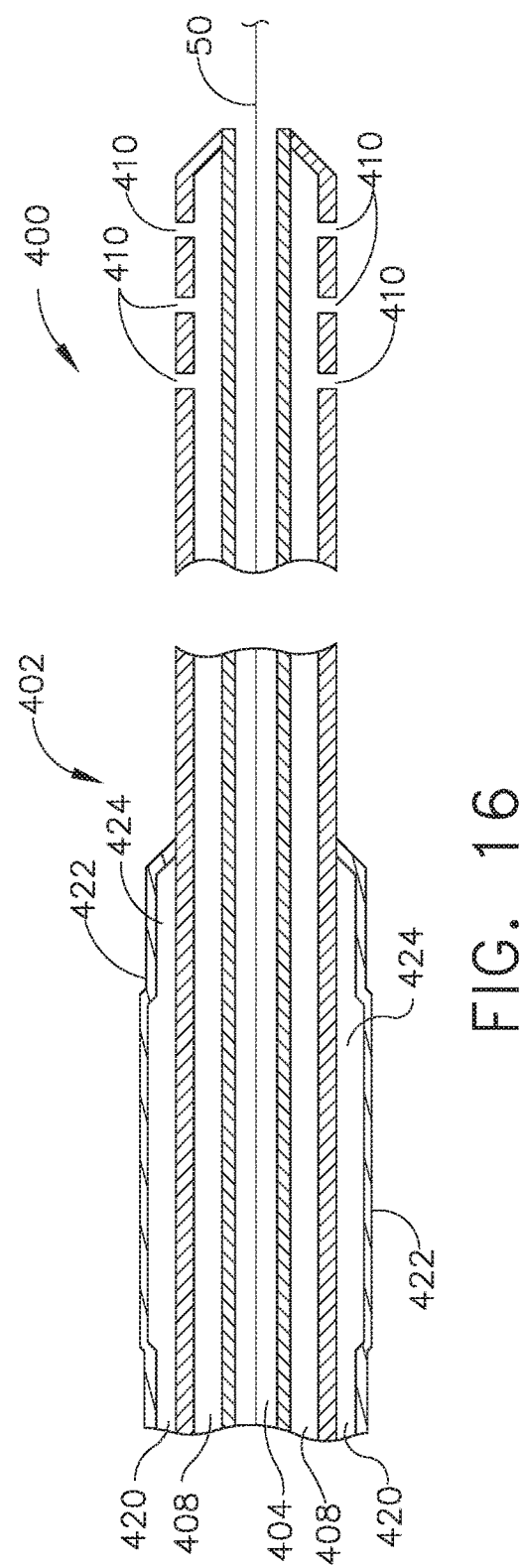

APPARATUS AND METHOD FOR IRRIGATING SINUS CAVITY

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, issued as U.S. Pat. No. 9,155,492 on Oct. 13, 2015, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now abandoned, the disclosure of which is incorporated by reference herein. An example of such an illuminating guidewire is the Relieva Luma Sentry™ Sinus Illumination System by Acclarent, Inc. of Menlo Park, Calif. Another guidewire may be provided in accordance with the teachings of U.S. patent application Ser. No. 14/835,108, entitled "Guidewire with Navigation Sensor", filed Aug. 25, 2015, published as U.S. Pub. No. 2016/0310041 on Oct. 27, 2016, the disclosure of which is incorporated by reference herein.

In some balloon sinuplasty procedures, the sinus cavity is irrigated with saline or some other fluid. In some instances, this irrigation may result in patient discomfort, as the irrigation fluid may tend to run down the patient's throat. One way in which the irrigation fluid may be managed includes the use of an absorbent member with a suction conduit, where the absorbent member is positioned in the posterior choana or the nasopharynx. An example of such a fluid management approach is described in U.S. Pat. No. 9,408,955, entitled "Nasal Fluid Management Device," issued Aug. 9, 2016. It may be desirable to use other kinds of devices and techniques to draw away irrigation fluids. While several systems and methods have been made and used to dilate, irrigate and suction, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 1 depicts a side elevational view of an exemplary dilation catheter system;

FIG. 3 depicts a detailed side elevational view of the illuminating guide wire of FIG. 2A;

FIG. 4 depicts a detailed side cross-sectional view of the illuminating guidewire of FIG. 2A;

FIG. 16 depicts an exemplary alternative catheter for occluding an ostium, and irrigating and suctioning a paranasal sinus cavity.

Figure 2A:
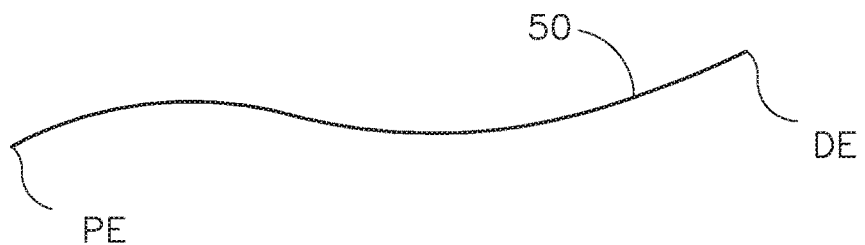
FIG. 2A depicts a side elevational view of an exemplary illuminating guidewire of the dilation catheter system of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

Figure 2B:
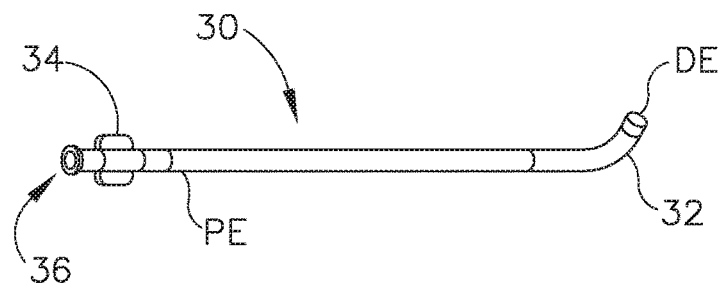
FIG. 2B depicts a side elevational view of an exemplary guide catheter of the dilation catheter system of FIG. 1.
Figure 2C:
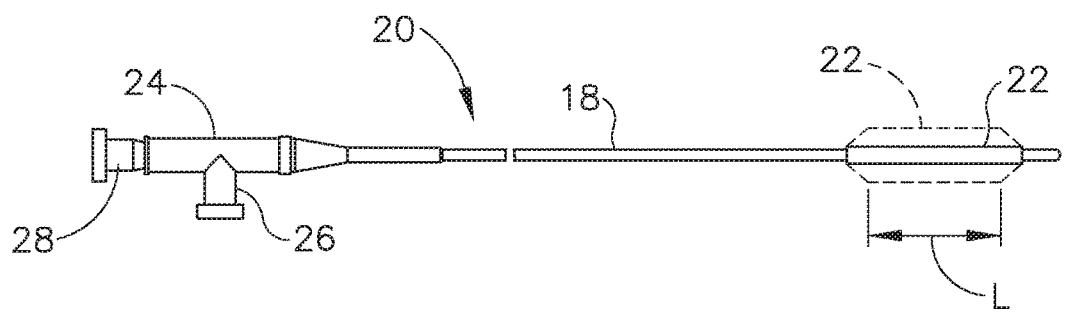
FIG. 2C depicts a side elevational view of an exemplary dilation catheter of the dilation catheter system of FIG. 1.

As best seen in FIG. 2C, the distal end (DE) of dilation catheter (20) includes an inflatable dilator (22). The proximal end (PE) of dilation catheter (20) includes a grip (24), which has a lateral port (26) and an open proximal end (28). A hollow-elongate shaft (18) extends distally from grip. Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif.

Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, issued as U.S. Pat. No. 9,155,492 on Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

II. Overview of Exemplary Endoscope

Figure 5:
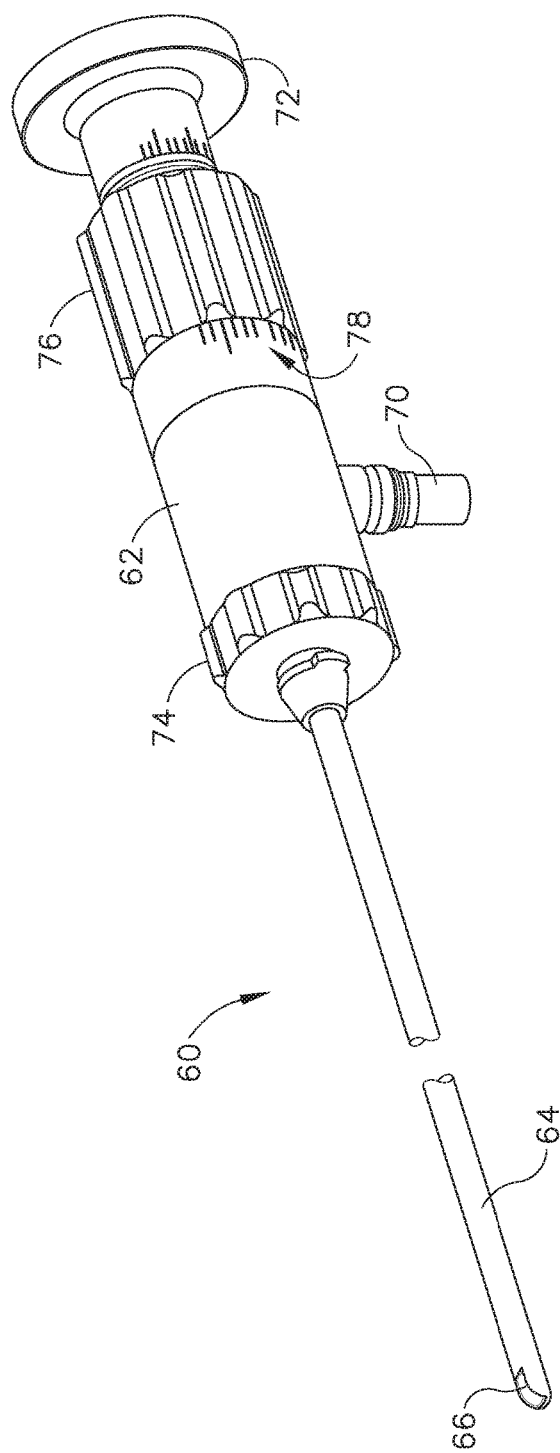
FIG. 5 depicts a perspective view of an exemplary endoscope suitable for use with the dilation catheter system of FIG. 1.
Figure 6:
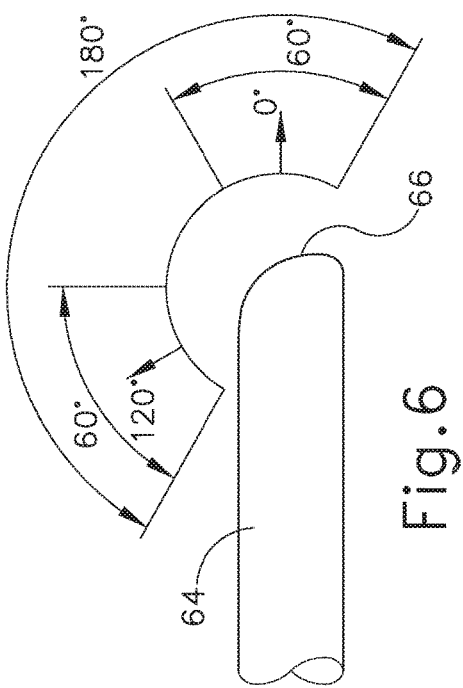
FIG. 6 depicts a side elevational view of the distal end of the endoscope of FIG. 5, showing an exemplary range of viewing angles.

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

III. Exemplary Method for Dilating Ostium of a Maxillary Sinus

FIGS. 7A-7E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 7A:
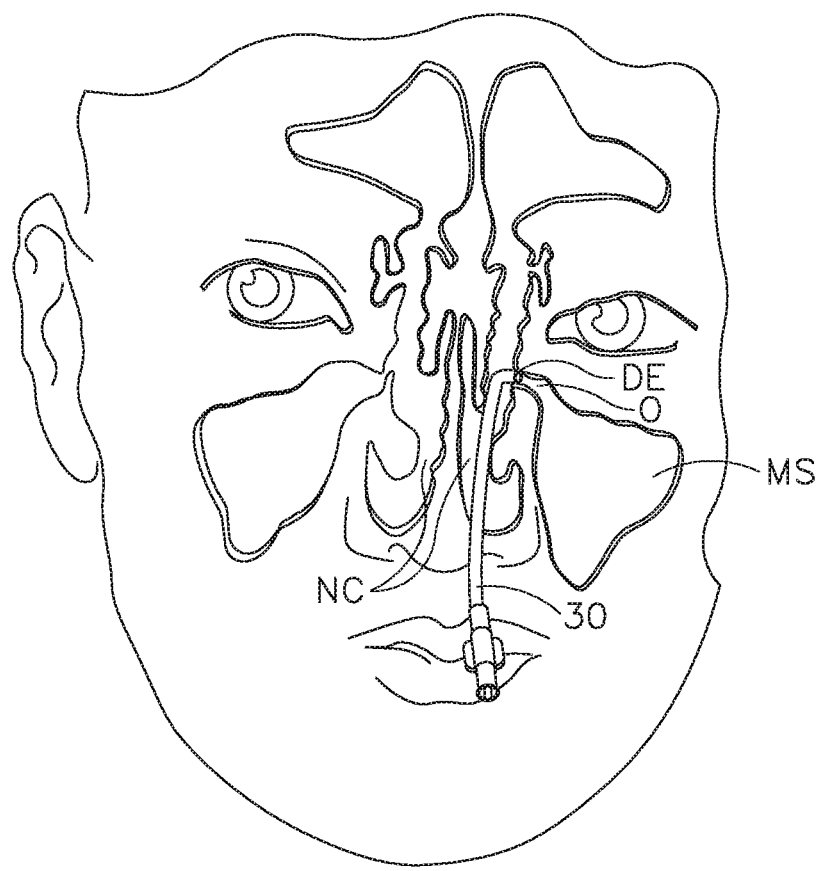
FIG. 7A depicts a front view of the guide catheter of FIG. 2B positioned adjacent an ostium of the maxillary sinus.
Figure 7C:
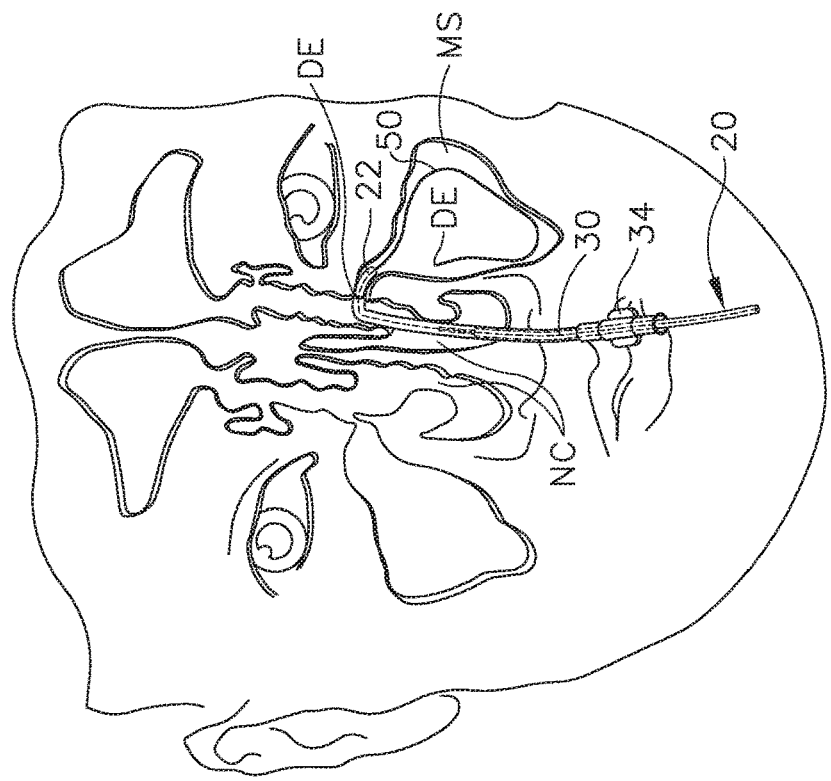
FIG. 7C depicts a front view of the guide catheter of FIG. 2B positioned adjacent an ostium of the maxillary sinus, with the illuminating guidewire of FIG. 2A translated further distally relative to the guide catheter and into the maxillary sinus.
Figure 7B:
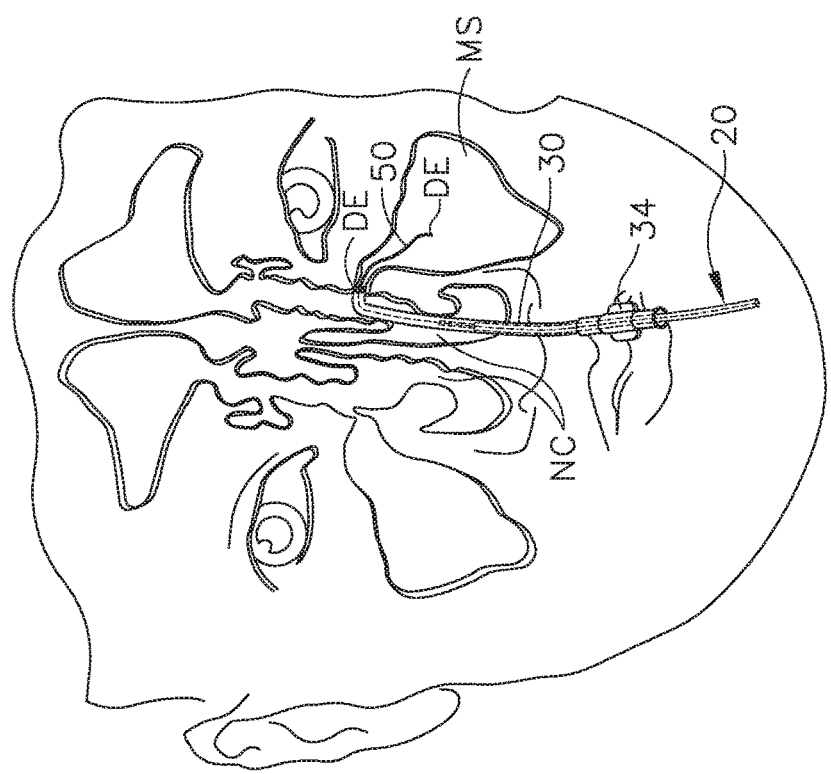
FIG. 7B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus.

In the procedure of the present example, guide catheter (30) may be inserted transversally and advanced through the nasal cavity (NC) to a position within or near the targeted anatomical passageway to be dilated, the sinus ostium (O), as shown in FIG. 7A. Inflatable dilator (22) and the distal end of guidewire (50) may be positioned within or proximal to bent distal end (32) of guide catheter (30) at this stage. This positioning of guide catheter (30) may be verified endoscopically with an endoscope such as endoscope (60) described above and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 7B and 7C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 7D:
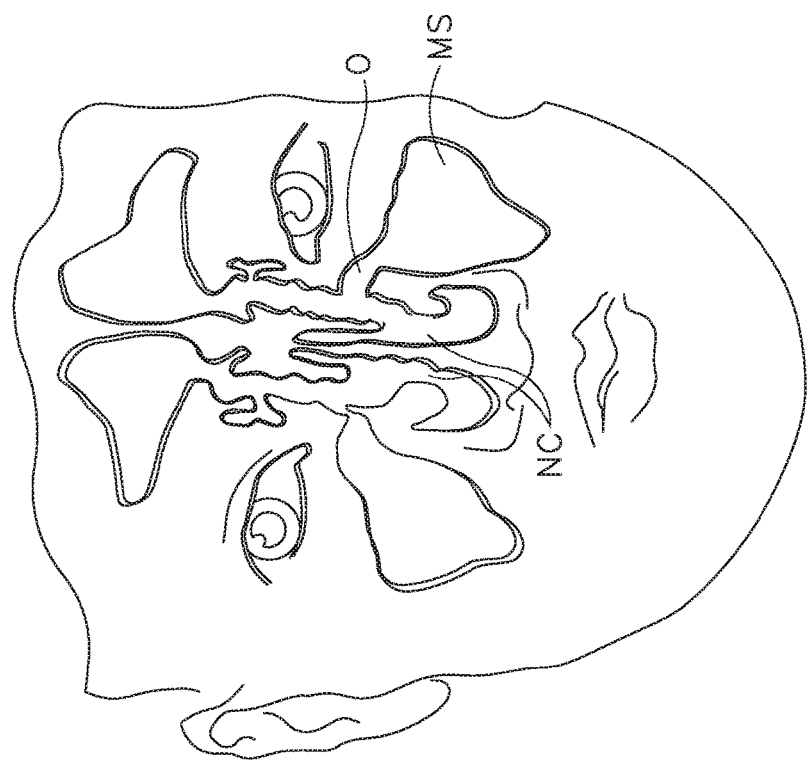
FIG. 7D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.
Figure 7E:
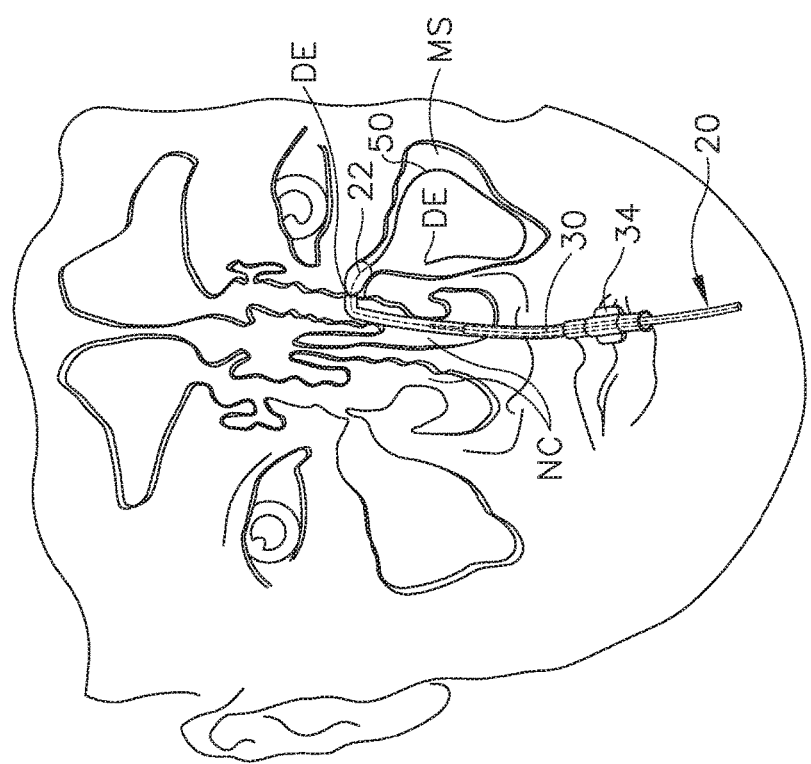
FIG. 7E depicts a front view of an ostium of the maxillary sinus, with the ostium having been enlarged by inflation of the balloon of FIG. 7D.

As shown in FIG. 7C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 7D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 7E.

IV. Exemplary Dilating, Occluding, Irrigating and Suctioning Catheter

Figure 8:
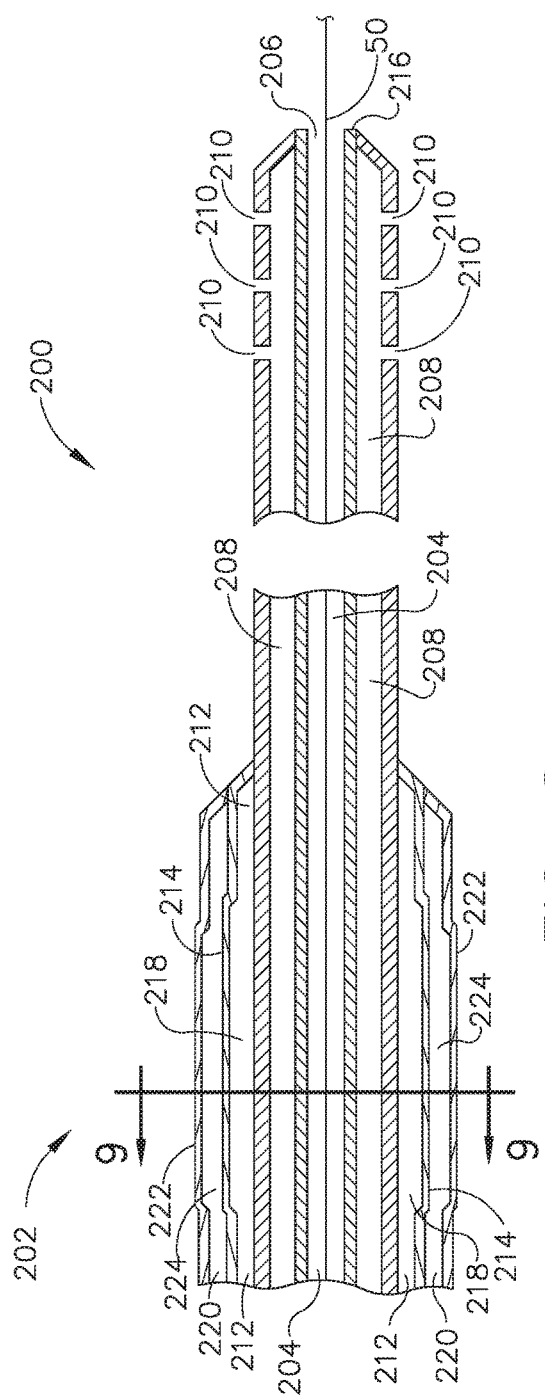
FIG. 8 depicts a side cross-sectional view of distal end of an exemplary dilation and irrigation catheter that may be used in the system of FIG. 1, in place of the dilation catheter of FIG. 2C.

FIG. 8 depicts the distal end (202) of an exemplary catheter (200) that is configured to dilate, occlude, irrigate and suction an anatomical passageway and cavity, such as a paranasal sinus. Catheter (200) is configured as an elongate flexible tube that extends from its proximal end, which may be connected to a handle, to distal end (202). It should be understood that the proximal end may include four fluid ports. In particular, the proximal end may include a first inflation port, a second inflation port, a suction port, and an irrigation fluid port. The purpose and function of such ports will be apparent from the below teachings.

Figure 9:
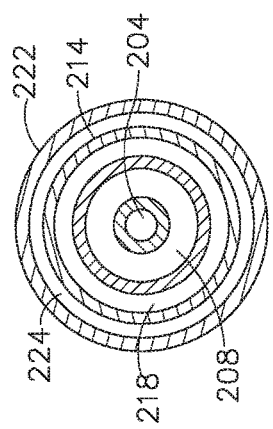
FIG. 9 depicts a cross-sectional view of the distal end of the catheter of FIG. 8 taken along line 9-9 of FIG. 8.

Referring also to FIG. 9, which illustrates a concentrically arranged plurality of lumens, catheter (200) includes centrally disposed first lumen (204) which terminates at distal end opening (206) at tip (216) of catheter (200). First lumen (204) is in fluid communication with the region outside of catheter (200) through opening (206). Surrounding first lumen (204) is second lumen (208). It should be understood that first lumen (204) may be in fluid communication with a suction port at the proximal end of catheter (200), such that suction may be communicated via first lumen (204) and opening (206). It should also be understood that first lumen (204) may slidably receive a guidewire, such as guidewire (50) described above.

Second lumen (208) is closed at its distal end and has a plurality of irrigation ports (210) provided through its sidewall. It should be understood that second lumen (208) may be in fluid communication with an irrigation port at the proximal end of catheter (200), such that irrigation fluid may be communicated via second lumen (208) and irrigation ports (210). By way of example only, irrigation ports (210) may be configured and operable in accordance with at least some of the teachings of U.S. Pub. No, 2008/0183128, entitled "Methods, Devices and Systems for Treatment and/or Diagnosis of Disorders of the Ear, Nose, and Throat," published Jul. 31, 2008, now abandoned, the disclosure of which is incorporated by reference herein.

Third lumen (212) surrounds second lumen (208), terminating at inflatable dilator (214) which is spaced proximally from the tip (216) of catheter (200). Interior (218) of dilator (214) is in fluid communication with third lumen (212). Dilator (214) may be selectively inflated and deflated by communicating inflating fluid along third lumen (212) via a third lumen port (not shown), or the first inflation port referred to above, located at the proximal end of catheter (200), which is in fluid communication with third lumen (212) and connectible to a source of inflating fluid having a suitable pressure. Dilator (214) is configured to transition between a non-expanded configuration and an expanded configuration. Dilator (214) is configured to fit in an ostium of a paranasal sinus in the non-expanded configuration. The fluid pressure within third lumen (212) may be increased up to a range of pressure suitable to dilate an ostium. Dilator (214) of the present example is formed of a flexible yet non-compliant material. Various suitable kinds of materials that may be used to form dilator (214) will be apparent to those of ordinary skill in the art in view of the teachings herein.

Fourth lumen (220) surrounds third lumen (212), terminating at occluding balloon (222) which is spaced from the tip (216) of catheter (200). Occluding balloon (222) defines interior (224) in which dilator (214) is disposed aligned with occluding balloon (222), and is in fluid communication with fourth lumen (220). Occluding balloon (222) may be selectively inflated and deflated by communicating fluid along fourth lumen (212) via a fourth lumen port (not shown), or the second inflation port referred to above, located at the proximal end of catheter (200), which is in fluid communication with fourth lumen (220) and connectible to a source of inflating fluid having a suitable pressure. Occluding balloon (222) is configured to transition between a non-expanded configuration and an expanded configuration. Occluding balloon (222) is configured to fit in an ostium of a paranasal sinus in the non-expanded configuration. The fluid pressure within fourth lumen (220) may be increased up to a range of pressure suitable to urge the expanded occluding balloon (222) into adequate sealing engagement with an ostium. Occluding balloon (222) is compliant in the present example, for example at least 10% compliant, and may be made of any material, such as Pebax or polyurethane, etc., which is suitable to create a seal around an ostium for a range of fluid pressure within fourth lumen (220), such as from 2 Atm to 20 Atm.

Lumens (204, 208, 212, 220) may be made out of any suitable material, such as polymers Nylon 12 or Pebax. Various suitable materials that may be used to form lumens (204, 208, 212, 220) will be apparent to those of ordinary skill in the art in view of the teachings herein. In addition, various suitable ways in which dilator (214) may be secured to third lumen (212), and various suitable ways in which occluding balloon (222) may be secured to fourth lumen (220), will be apparent to those of ordinary skill in the art in view of the teachings herein.

Figure 10:
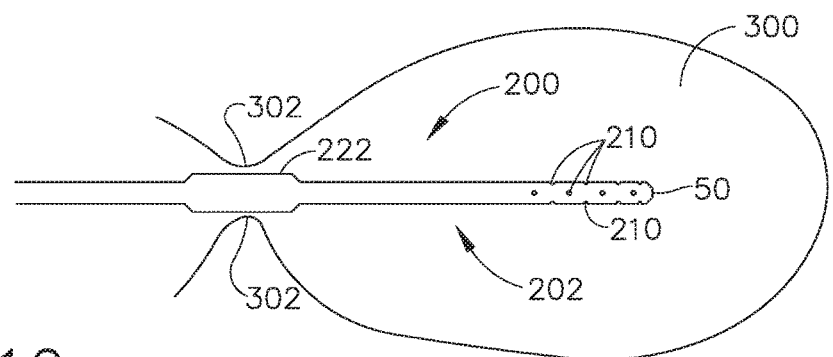
FIG. 10 depicts a side view of the distal end of the catheter of FIG. 8 disposed through an ostium and in a paranasal sinus cavity.

Catheter (200) may be used to dilate and occlude an ostium leading to an anatomical cavity, such as a paranasal sinus cavity, and irrigate and suction that cavity. FIGS. 10-15 depict an exemplary use of catheter (200). FIG. 10 shows the distal end (202) of catheter (200) as having entered a paranasal sinus cavity (300) through ostium (302), guided by steering the end, such as with the aid of guidewire (50) and/or guide catheter (30), and pushing on a proximal end of catheter (200) to advance distal end (202) distally through ostium (302) and into paranasal sinus cavity (300). Catheter (200) is disposed such that occluding balloon (222) and underlying dilator (214) is aligned with ostium (302) so that ostium (302) may be dilated. In some alternative versions, dilator (214), occluding balloon (222) and associated lumens (212) and (220) may be configured to be moveable along the axial length of catheter (200), such that the operator may selectively adjust the distance between tip (216) of catheter (200) and the position of dilator (214)/occluding balloon (222).

Figure 11:
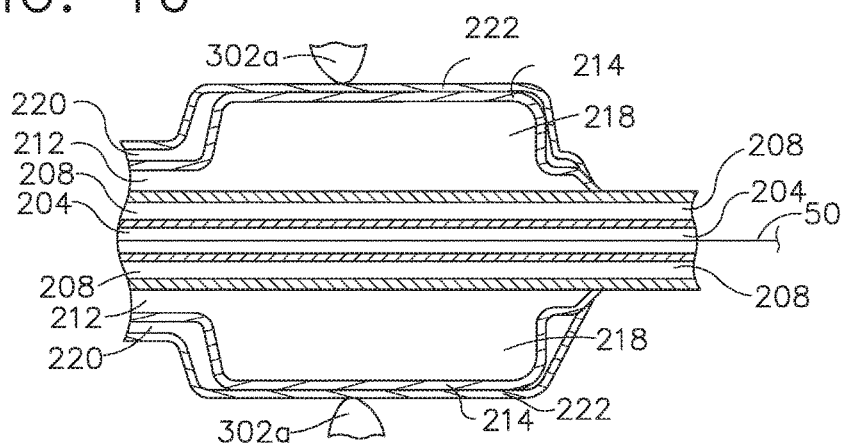
FIG. 11 depicts a side cross-sectional view of the distal end of the catheter of FIG. 8, with a dilation balloon in an expanded state, thereby dilating the ostium of FIG. 10.
Figure 12:
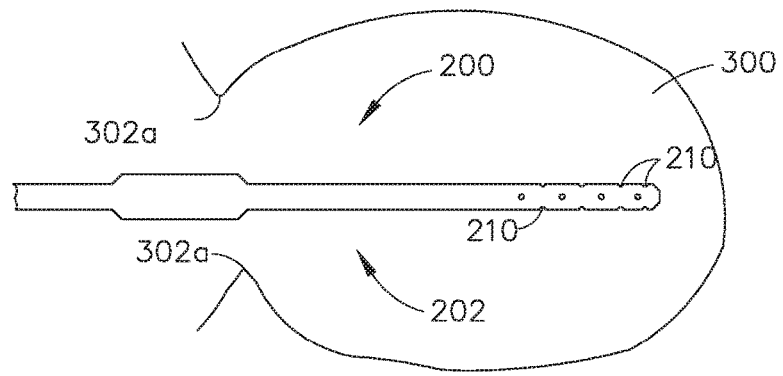
FIG. 12 depicts a side view of the distal end of the catheter of FIG. 8 disposed through the dilated ostium of FIG. 11 and in the paranasal sinus cavity.

As illustrated in FIG. 11, once aligned with ostium (302), dilator (214) is inflated by communicating fluid (e.g., saline) along third lumen (212). Dilator (214) expands as a result of the increased pressure within third lumen (212) and interior (218) resulting in dilated ostium (302a). Occluding balloon (222) expands with dilator (214) as a result of the inflation of dilator (214), bearing directly against ostium (302), but fourth lumen (220) is not pressurized by fluid via the fourth lumen port. Nevertheless, in some instances, it may be desirable to allow venting of fourth lumen (220) during the stages at which dilator (214) is inflated and deflated. When dilation is completed, fluid is withdrawn from interior (218) via third lumen (212), collapsing dilator (214) down and returning catheter (200) to its unexpanded configuration, as seen in FIG. 12. FIG. 12 illustrates guidewire (50) withdrawn from first lumen (204) while catheter (200) remains in the same location. It should be understood that occluding balloon (222) may resiliently return to an unexpanded configuration as dilator (214) returns to an unexpanded configuration.

Figure 13:
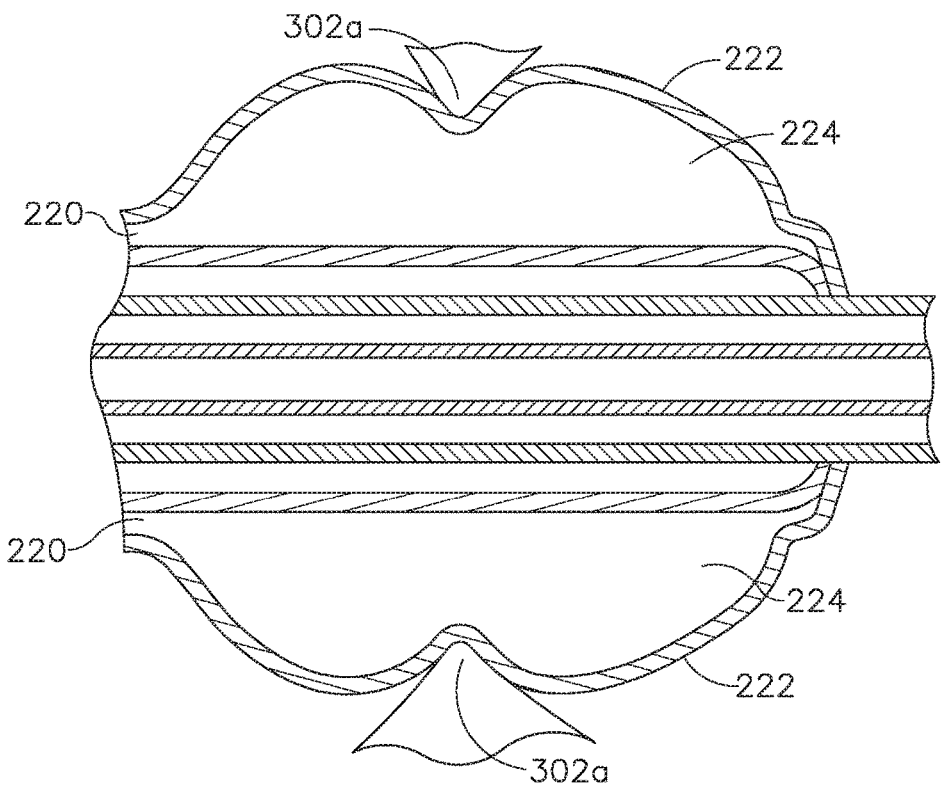
FIG. 13 depicts a side cross-sectional view of the distal end of the catheter of FIG. 8, with an occlusion balloon in an expanded state, thereby occluding the dilated ostium of FIG. 11.

As illustrated in FIG. 13, without moving catheter (200), following dilation of ostium (302), occluding balloon (222) is inflated by communicating fluid (e.g., saline) along fourth lumen (220). Occluding balloon (222) expands as a result of the increased pressure within fourth lumen (220) and interior (224) and is thereby urged into adequate sealing engagement against dilated ostium (302a). Dilator (214) remains in its unexpanded configuration and third lumen (212) is not pressurized via the third lumen port. Since occluding balloon (222) is compliant, occluding balloon (222) will eventually deform around the dilated ostium (302a) to provide the sealing configuration shown in FIG. 13. Moreover, occluding balloon (222) will not further dilate ostium (302a), even though occluding balloon (222) will bear against dilated ostium (302a) to some degree when occluding balloon (222) is expanded to reach the sealing configuration shown in FIG. 13.

With occluding balloon (222) deployed to occlude dilated ostium (302a), catheter (200) may be used to irrigate and suction paranasal sinus cavity (300) simultaneously. To the extent that guidewire (50) has not already been removed from first lumen (204) at this point, the operator may remove guidewire (50) from first lumen (204) before initiating suction and irrigation. A flow of irrigation fluid may be introduced into second lumen (208) via a second lumen port (not shown) located at the proximal end of catheter (200), which is in fluid communication with second lumen (208) and connectible to a source of irrigating fluid. The irrigation fluid may comprise diagnostic or therapeutic substances. Examples of such diagnostic or therapeutic substances include, but are not limited to: contrast agents, pharmaceutically acceptable salt or dosage form of an antimicrobial agent (e.g., antibiotic, antiviral, anti-parasitic, antifungal, etc.), a corticosteroid or other anti-inflammatory (e.g., an NSAID), a decongestant (e.g., vasoconstrictor), a mucous thinning agent (e.g., an expectorant or mucolytic), an anesthetic agent with or without vasoconstrictor (e.g., Xylocaine with or without epinephrine, Tetracaine with or without epinephrine), an analgesic agent, an agent that prevents of modifies an allergic response (e.g., an antihistamine, cytokine inhibitor, leucotriene inhibitor, IgE inhibitor, immunomodulator), an allergen or another substance that causes secretion of mucous by tissues, anti-proliferative agents, hemostatic agents to stop bleeding, cytotoxic agents e.g. alcohol, and biological agents such as protein molecules, stem cells, genes or gene therapy preparations.

Figure 14:
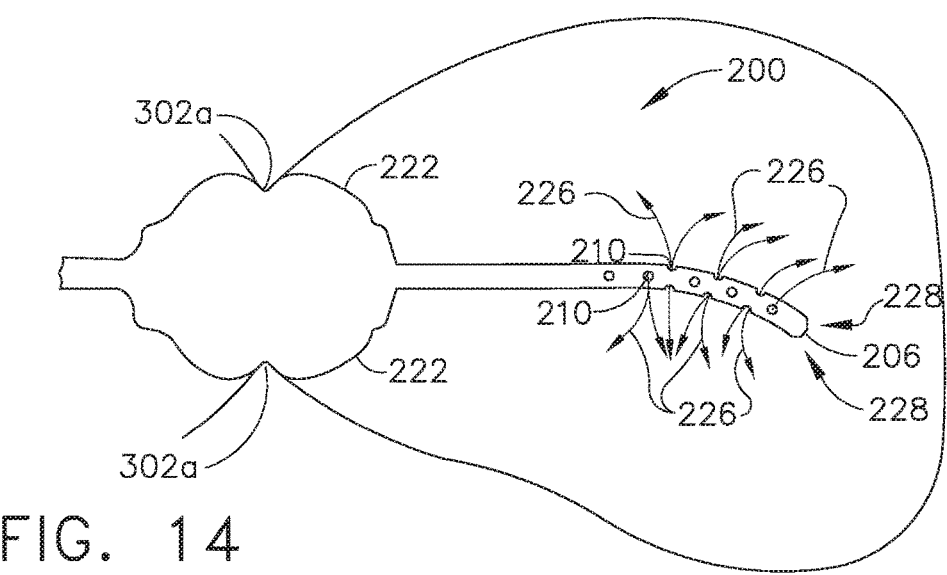
FIG. 14 depicts a side view of the distal end of the catheter of FIG. 8 occluding the dilated ostium of FIG. 11 and irrigating and suctioning the paranasal sinus cavity.

As seen in FIG. 14, the irrigation fluid is delivered into paranasal sinus cavity (300) through irrigation ports (210) in catheter (200) at distal end (202). Any suitable number, configuration and orientation of irrigation ports (210) may be used. By way of example only, at least two, three, four, or more irrigation ports (210) may be provided to direct irrigation spray (226) in different directions radially from distal end (202). Further in this regard, irrigation ports (210) can be formed in a spiral pattern about distal end (202), or other pattern, so that no two openings are aligned with one another in a direction perpendicular to the longitudinal axis. Irrigation ports (210) are provided to create vortices or turbulent flow of irrigation fluid as it is ejected from irrigation ports (210). Irrigation ports (210) are placed so as to eject fluid in radially varying directions to produce the turbulent flow vortices in substantially all direction around the circumference of catheter (200) where irrigation ports (210) are located. The turbulent flow/vortices are further propagated when catheter (210) deliver sprays in a small anatomical space, such as a paranasal sinus cavity, since the spray hits against one or more walls defining the cavity, further disturbing the flow and increasing the turbulence. Although irrigation ports (210) are illustrated adjacent tip (216), they may be disposed at any location between occluding balloon (222) and tip (216) suitable to irrigate paranasal sinus cavity (300).

Simultaneous with the irrigation of paranasal sinus cavity (300) via irrigation ports (210), a vacuum is applied to first lumen (204) via a first lumen port (not shown) located at the proximal end of catheter (200), which is in fluid communication with first lumen (204) and connectable to a vacuum source. The suction may range from 0.038 inches water to 0.070 inches water, or any other suitable level of suction. As a result, fluid in paranasal sinus cavity (300) is suctioned out through opening (206), functioning as a suction port, indicated by arrows (228). With dilated ostium (302a) occluded, fluid is suctioned out through opening (206) at a rate sufficient to keep up with the flow of irrigation fluid out of irrigation ports (210) to prevent pressure and fluid from building up within paranasal sinus cavity (300). Opening (206), as well as first lumen (204), may be of any suitable size, such as 0.038-0.050 inches in diameter. The sidewall of first lumen (204) is configured not to collapse or otherwise deleteriously reduce the cross sectional area of first lumen (204) as a result of the suctioning of fluid through first lumen (204) or the pressure of fluid in second lumen (208). It should be understood that the occlusion of ostium (302a) by expanded occluding balloon (222) will prevent the irrigation fluid from escaping sinus cavity via ostium (302a) during the irrigation process shown in FIG. 14.

Figure 15:
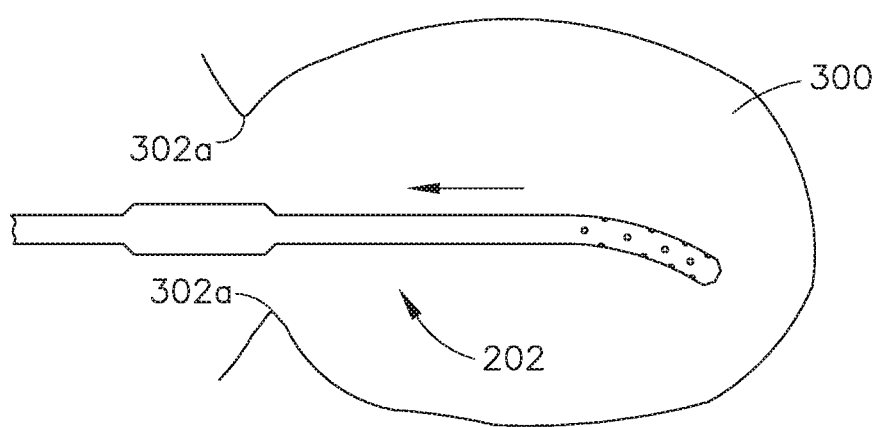
FIG. 15 depicts a side view of the distal end of the catheter of FIG. 8 with the occlusion and dilation balloons in a non-expanded state, following the occlusion, irrigation, and suction of the paranasal sinus cavity, and prior to removal from the paranasal sinus cavity.

When irrigation and suctioning has concluded, fluid is withdrawn from interior (224) via third lumen (212), collapsing occluding balloon (222) down and returning catheter (200) to its unexpanded configuration, as seen in FIG. 15. Distal end (202) may then be withdrawn proximally from paranasal sinus cavity (300) and dilated ostium (302a). At this stage, ostium (302a) remains dilated; and paranasal sinus cavity (300) has been irrigated and suctioned, without any irrigation fluid flowing into the patient's throat.

It should be understood from the foregoing that catheter (200) of the present example enables an operator to perform dilation, irrigation, and suction, all with one single catheter (200). Moreover, catheter (200) of the present example enables an operator to perform dilation, irrigation, and suction without the operator having to longitudinally reposition catheter (200) in the patient between any of the steps of dilation, irrigation, and suction.

V. Exemplary Alternative Occluding, Irrigating and Suctioning Catheter

FIG. 16 depicts distal end (402) of an exemplary alternative catheter (400), similar to catheter (200), which is configured to occlude, irrigate, and suction but not dilate. Similar to catheter (200), catheter (400) includes first lumen (404) which corresponds to the structure and function of first lumen (204) as described above. Catheter (400) also includes second lumen (408) and a plurality of openings (410), which correspond to the structures and functions of second lumen (208) and irrigation ports (210), respectively, as described above.

Catheter (400) does not have a dilator, nor its corresponding lumen, in this particular example. Third lumen (420) surrounds second lumen (408), terminating at occluding balloon (422) having interior (424). Third lumen (420), occluding balloon (422) and interior (424) correspond to the structures and functions of fourth lumen (220), occluding balloon (222) and interior (224), respectively as described above.

Catheter (400) may be used to occlude an ostium leading to an anatomical cavity, and irrigate and suction that cavity in the manner as catheter (200) is used to occlude an ostium, and irrigate and suction a paranasal sinus cavity, as described above. If necessary, the ostium may be first dilated using a dilation catheter, followed by advancing catheter (400) through the dilated ostium and into the paranasal sinus cavity to be irrigated and suctioned. For instance, an operator may first use dilation catheter (20) to dilate the sinus ostium, remove dilation catheter (20) from guide catheter (30), insert catheter (400) through guide catheter (30) to position occluding balloon (422) in the dilated ostium, then provide irrigation and suction to the corresponding paranasal sinus cavity via catheter (400). It should also be understood that, in some instances, catheter (400) may be used to irrigate and suction a paranasal sinus cavity without first having to dilate an ostium or other passageway leading to the paranasal sinus cavity. Moreover, catheter (400) may be used to irrigate and suction other anatomical structures, such that the utility of catheter (400) is not necessarily limited to paranasal sinus cavities. Various other suitable ways in which catheter (400) may be used will be apparent to those of ordinary skill in the art in view of the teachings herein.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A device comprising a catheter having a proximal end and a distal end, wherein at least a portion of the catheter is sized to pass through a nasal cavity and through a sinus ostium to enter a paranasal sinus cavity, the catheter comprising: (i) an occluding balloon disposed at the distal end, wherein the occluding balloon is configured to transition between a non-expanded configuration and an expanded configuration, wherein the occluding balloon is configured to fit in the ostium in the non-expanded configuration, and wherein the occluding balloon is configured to sealingly engage the ostium in the expanded configuration, (ii) a plurality of irrigation ports disposed at the distal end, wherein the occluding balloon is located proximal to the irrigation ports, and (iii) a suction port disposed at the distal end, wherein the occluding balloon is located proximal to the suction port.

Example 2

The device of Example 1, wherein the catheter further comprises a dilator disposed at the distal end, wherein the dilator is configured to transition between a non-expanded configuration and an expanded configuration, wherein the dilator is configured to fit in the ostium in the non-expanded configuration, and wherein the dilator is configured to dilate the ostium expanded configuration.

Example 3

The device of Example 2, wherein the dilator is formed of a non-compliant material.

Example 4

The device of any one or more of Examples 2 through 3, wherein the occluding balloon defines an interior, and wherein the dilator is disposed in the interior of the occluding balloon.

Example 5

The device of any one or more of Examples 2 through 4, wherein the dilator is longitudinally aligned with the occluding balloon.

Example 6

The device of any one or more of Examples 2 through 5, wherein the catheter further comprises a plurality of lumens, each of the dilator, the occluding balloon, the plurality of irrigation ports and the suction port having an associated lumen of the plurality of lumens.

Example 7

The device of Example 6, wherein the plurality of lumens is concentrically disposed.

Example 8

The device of any one or more of Examples 1 through 7, wherein the occluding balloon is formed of a compliant material.

Example 9

The device of any one or more of Examples 1 through 8, wherein the distal end terminates at a tip, and wherein the plurality of irrigation ports is disposed between the occluding balloon and the tip.

Example 10

The device of Example 9, wherein the plurality of irrigation ports is disposed adjacent the tip.

Example 11

The device of any one or more of Examples 1 through 10, wherein the catheter comprises a first lumen extending between the proximal end and the distal end, wherein the first lumen is in fluid communication with the suction port, and wherein the first lumen is connectable to a vacuum source.

Example 12

The device of Example 11, wherein the catheter comprises a second lumen extending between the proximal end and the distal end, wherein the second lumen is in fluid communication with the plurality of irrigation ports, and wherein the second lumen is connectable to a source of irrigation fluid.

Example 13

The device of any one or more of Examples 11 through 12, wherein the second lumen surrounds the first lumen at least between the proximal end and the distal end.

Example 14

The device of any one or more of Examples 1 through 13, wherein the occluding balloon defines an interior, wherein the catheter comprises a lumen extending between the proximal end and the distal end, wherein the lumen is in fluid communication with the interior, and wherein the lumen is connectable to a source of fluid.

Example 15

The device of any one or more of Examples 1 through 14, wherein the catheter comprises a plurality of lumens, each of the occluding balloon, the plurality of irrigation ports and the suction port having an associated lumen of the plurality of lumens.

Example 16

The device of Example 15, wherein the plurality of lumens is concentrically disposed.

Example 17

A device comprising an elongate catheter having a proximal end and a distal end, wherein at least a portion of the catheter is sized to pass through a nasal cavity and through a sinus ostium to enter a paranasal sinus cavity, the catheter comprising: (i) a first lumen extending between the proximal end and terminating at the distal end in communication with a distal end opening, (ii) a first port disposed at the proximal end, wherein the first port is in fluid communication with the first lumen, and wherein the first port is connectable to a vacuum source, (iii) a second lumen extending between the proximal end and terminating at the distal end, wherein the second lumen is in fluid communication with a plurality of irrigation ports disposed through a sidewall of the second lumen at the distal end, (iv) a second port disposed at the proximal end, wherein the second port is in fluid communication with the second lumen, and wherein the second port is connectable to a source of irrigation fluid, (v) a third lumen extending between the proximal end and the distal end, (vi) a third port disposed at the proximal end, wherein the third port is in fluid communication with the third lumen, and wherein the third port is connectable to a source of fluid, and (vii) an occluding balloon disposed at the distal end, wherein the occluding balloon defines an interior, wherein the interior is in fluid communication with the third lumen, wherein the occluding balloon is configured to transition between a non-expanded configuration and an expanded configuration, wherein the occluding balloon is configured to fit in the ostium in the non-expanded configuration, and wherein the occluding balloon is configured to sealing engage the ostium in the expanded configuration.

Example 18

The device of Example 17, wherein the catheter further comprises: (a) a fourth lumen extending between the proximal end and the distal end; and (b) a dilator disposed at the distal end, wherein the dilator defines an interior, wherein the interior is in fluid communication with the fourth lumen, wherein the dilator is configured to transition between a non-expanded configuration and an expanded configuration, wherein the dilator is configured to fit in the ostium in the non-expanded configuration, and wherein the dilator is configured to dilate the ostium expanded configuration.

Example 19

A method for irrigating a paranasal sinus cavity, the method comprising: (a) advancing a distal end of a catheter through an ostium of a paranasal sinus cavity into the paranasal sinus cavity; (b) inflating an occluding balloon disposed on the catheter into sealing engagement with the ostium, thereby sealing the ostium; (c) applying a vacuum to the sinus through a distal end opening of the catheter while the ostium is sealed by the occluding balloon; (d) passing irrigation fluid through a plurality of injection ports disposed on the distal end while the ostium is sealed by the occluding balloon; and (e) suctioning the irrigation fluid from the sinus through the distal end opening while the ostium is sealed by the occluding balloon.

Example 20

The method of Example 19, comprising dilating the ostium by inflating a dilator disposed on the catheter.

VII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A device comprising a catheter having a proximal end and a distal end, wherein at least a portion of the catheter is sized to pass through a nasal cavity and through a sinus ostium to enter a paranasal sinus cavity, the catheter comprising:
   (i) a dilator disposed at the distal end, wherein the dilator is configured to transition between a non-expanded configuration and an expanded configuration, wherein the dilator is configured to fit the ostium in the non-expanded configuration, and wherein the dilator is configured to dilate the ostium in the expanded configuration,
   (ii) an occluding balloon disposed at the distal end, wherein the occluding balloon is configured to transition between a non-expanded configuration and an expanded configuration, wherein the occluding balloon is configured to fit in the ostium in the non-expanded configuration, and wherein the occluding balloon is configured to sealingly engage the ostium in the expanded configuration while the dilator is in the non-expanded configuration,
   (iii) a plurality of irrigation ports disposed in a sidewall at the distal end, wherein the occluding balloon is located proximal to the irrigation ports, (iv) a suction port disposed on a distal face of the distal end, proximate to the irrigation ports, wherein the occluding balloon is located proximal to the suction port, and
(v) a plurality of lumens, the plurality of lumens including:
  (i) a first lumen in fluid communication with the dilator,
  (ii) a second lumen in fluid communication with the occluding balloon,
  (iii) a third lumen in fluid communication with the irrigation ports, and
  (iv) a fourth lumen in fluid communication with the suction port,
  wherein the first, second, third, and fourth lumens are in fluid isolation relative to each other.

2. The device of claim 1, wherein the dilator is formed of a non-compliant material.

3. The device of claim 1, wherein the occluding balloon defines an interior, and wherein the dilator is disposed in the interior of the occluding balloon.

4. The device of claim 1, wherein the dilator is longitudinally aligned with the occluding balloon.

5. The device of claim 1, wherein the plurality of lumens are coaxial with each other.

6. The device of claim 1, wherein the occluding balloon is formed of a compliant material.

7. The device of claim 1, wherein the distal end terminates at a tip, and wherein the plurality of irrigation ports is disposed between the occluding balloon and the tip.

8. The device of claim 7, wherein the plurality of irrigation ports is disposed adjacent the tip.

9. The device of claim 1, wherein the third lumen surrounds the fourth lumen at least between the proximal end and the distal end.

10. A device comprising an elongate catheter having a proximal end and a distal end, wherein at least a portion of the catheter is sized to pass through a nasal cavity and through a sinus ostium to enter a paranasal sinus cavity, the catheter comprising:
  (i) a first lumen extending between the proximal end and terminating at the distal end in communication with a distal end opening,
  (ii) a first port disposed at the proximal end, wherein the first port is in fluid communication with the first lumen, and wherein the first port is connectable to a vacuum source,
  (iii) a second lumen extending between the proximal end and terminating at the distal end, wherein the second lumen is in fluid communication with a plurality of irrigation ports disposed through a sidewall of the second lumen at the distal end,
  (iv) a second port disposed at the proximal end, wherein the second port is in fluid communication with the second lumen, and wherein the second port is connectable to a source of irrigation fluid,
  (v) a third lumen extending between the proximal end and the distal end,
  (vi) a third port disposed at the proximal end, wherein the third port is in fluid communication with the third lumen, and wherein the third port is connectable to a source of fluid,
  (vii) a fourth lumen extending between the proximal end and the distal end,
  (viii) a fourth port disposed at the proximal end, wherein the fourth port is in fluid communication with the fourth lumen, and wherein the fourth port is connectable to a source of fluid,
  (ix) a dilator disposed at the distal end, wherein the dilator is configured to transition between a non-expanded configuration and an expanded configuration, wherein the dilator is configured to fit the ostium in the non-expanded configuration, and wherein the dilator is configured to dilate the ostium in the expanded configuration, wherein the dilator is in fluid communication with the third lumen, and
  (x) an occluding balloon disposed at the distal end, wherein the occluding balloon defines an interior, wherein the interior is in fluid communication with the fourth lumen, wherein the occluding balloon is configured to transition between a non-expanded configuration and an expanded configuration, wherein the occluding balloon is configured to fit in the ostium in the non-expanded configuration, and wherein the occluding balloon is configured to sealingly engage the ostium in the expanded configuration.

11. The device of claim 1, wherein the dilator is dilator is configured to dilate the ostium in the expanded configuration by remodeling bone forming the ostium.

12. The device of claim 1, wherein the occluding balloon is configured to provide fluid isolation between an interior space of the occluding balloon and a space exterior to the occluding balloon.

* * * * *